United States Patent [19]
Mangelsdorf et al.

[11] Patent Number: 5,707,800
[45] Date of Patent: Jan. 13, 1998

[54] RETINOIC ACID RESPONSE ELEMENTS AND ASSAYS EMPLOYING SAME

[75] Inventors: David John Mangelsdorf, San Diego; Ronald M. Evans; Kazuhiko Umesono, both of La Jolla; Steven A. Kliewer, San Diego, all of Calif.

[73] Assignee: The Salk Institute for Biological Studies, La Jolla, Calif.

[21] Appl. No.: 346,342

[22] Filed: Nov. 28, 1994

Related U.S. Application Data

[63] Continuation of Ser. No. 671,044, Mar. 18, 1991, abandoned.

[51] Int. Cl.$^6$ .............................. C12Q 1/68; C12P 21/06; C12N 15/00; C07H 17/00
[52] U.S. Cl. .............................. 435/6; 435/7.8; 435/7.21; 435/7.2; 435/367; 435/365; 435/358; 435/357; 435/349; 435/348; 435/325; 435/252.3; 435/320.1; 435/78; 435/69.1; 536/24.1; 536/23.1; 536/23.2
[58] Field of Search .................. 536/24.1, 23.1; 435/69.1, 240.1, 320.1, 7.8, 6; 936/6, 33, 34, 36

[56] References Cited

PUBLICATIONS

Chandler et al., DNA Sequences Bound Specifically by Glucocorticoid Receptor In Vitro Render a Heterologous Promoter Hormone Responsive In Vivo, Cell 33:489 499 (1983).
Green and Chambon, Nuclear receptors enhance our understanding of transcription regulation, Trends in Genetics 4:309–314 (1988).
Klein–Hitpass et al., A 13 bp palindrome is a functional estrogen responsive element and interacts specifically with estrogen receptor, Nucleic Acids Research 16:647–663 (1988).
Mangelsdorf et al., Nuclear receptor that identifies a novel retinoic acid response pathway, Nature 345:224–229 (1990).
Miyajima et al., Identification of two novel members of erbA superfamily by molecular cloning: the gene products of the two are highly related to each other, Nucl.Acids Res. 16:11057–11074 (1988).
Wang et al., COUP transcription factor is a member of the steroid receptor superfamily, Nature 340:163–166 (1989).
Oro et al., Relationship between the product of the Drosophila ultraspiracle locus and the vertebrate retinoid X receptor, Nature 347:298–301 (1990).
Mlodzik et al., The Drosophila seven–up Gene, a Member of the Steroid Receptor Gene Superfamily, Controls Photoreceptor Cell Fates, Cell 60:211–224 (1990).
Sladek et al., Liver–enriched transcription factor HNF–4 is a novel member of the steroid hormone receptor superfamily, Genes & Development 4:2353–2365 (1990).
Ladias and Karathanasis, Regulation of the Apolipoprotein AI Gene by ARP-1, a Novel Member of the Steroid Receptor Superfamily, Science 251:561–565 (1991).
Hull et al. 1986 EMBO J. 5(12):3083–3090.
Sambrook et al. 1989 Molecular Cloning—A Laboratory Manual. CSHL Press, CSH, NY p. 11.7.

*Primary Examiner*—Karen C. Carlson
*Attorney, Agent, or Firm*—Gray Cary Ware & Freidenrich; Stephen E. Reiter; David F. Kleinsmith

[57] ABSTRACT

DNA segments have been discovered, and characterized by sequence, which are response elements operative to confer responsiveness to retinoic acid, or derivatives thereof, for the transcriptional activation of promoters in cells. By using transcriptional control regions comprising response elements of the present invention in combination with a functional promoter, it is now possible to provide recombinant DNA vectors containing a gene, the transcription (and, thereby, also expression) of which is under the control of a promoter, the transcriptional activity of which is responsive to (and increased by) retinoic acid or derivatives thereof.

72 Claims, 4 Drawing Sheets

RETINOIC ACID RESPONSE ELEMENTS AND ASSAYS EMPLOYING SAME

This application is a continuation of application Ser. No. 07/671,044, filed Mar. 18, 1991 now abandoned.

FIELD OF INVENTION

The present invention relates to the superfamily of nuclear receptors known as the steroid/thyroid hormone receptors and their cognate response elements. More particularly, the present invention relates to the discovery of novel response elements which may be used to control the transcriptional activity of promoters.

BACKGROUND OF THE INVENTION

A central question in eukaryotic molecular biology is how specific DNA-binding proteins bind regulatory sequences to influence cell function and fate. The steroid/thyroid hormone receptors form a superfamily of ligand-dependent transcription factors that are believed to play a part in such cell function and fate. For example, it is known that these receptors transduce extracellular hormonal signals to target genes that contain specific enhancer sequences (referred to as hormone-response elements, or HREs). Each receptor contains a ligand-binding domain and a DNA-binding domain. The receptor undergoes a conformational change when it binds ligand. This conformational change permits the receptor-ligand complex to bind its cognate response element and thereby regulate transcriptional activity of an associated promoter. Transcriptional activation of promoter drives transcription of an operatively associated structural gene.

Sequence comparison and mutational analyses of hormone receptors, such as the glucocorticoid receptor (GR), have identified functional domains responsible for transcriptional activation and repression, nuclear localization, DNA binding, and hormone binding. The DNA binding domain, which is required in order to activate transcription, consists of 66–68 amino acids of which about 20 sites, including nine cysteines ($C_1$ to $C_9$), are invariant among different receptors. The modular structure of members of this receptor superfamily allows the exchange of one domain for another to create functional, chimeric receptors.

The hormone response elements identified thus far are generally structurally related, but they are in fact functionally distinct. The response elements for GR [i.e., the glucocorticoid response element (GRE)], estrogen receptor [i.e., the estrogen response element (ERE)], and thyroid hormone receptor [i.e., the thyroid hormone response elements (TREs)] have been characterized in detail; they each consist of a palindromic pair of 'half sites' [Evans, Science 240, 889 (1988); Green and Chambon, Trends in Genetics 4, 309 (1988)]. With optimized pseudo- or consensus response elements, only two nucleotides per half site are different in GRE and ERE [Klock, et al., Nature 329, 734 (1987)]. On the other hand, identical half sites can be seen in ERE and TRE, but their spacing is different [Glass, et al., Cell 54, 313 (1988)]. Moreover, TRE has been shown to mediate transcriptional activation by transfected retinoic acid receptors (RARs) in CV-1 cells whereas non-transfected cells show no response. [Umesono et al., Nature 336, 262 (1988)]. In other words, both TR and RAR receptors can activate TREs.

Since the response elements for only a few of the members of the steroid/thyroid superfamily have thus far been described, the response elements for other members of the superfamily remain to be described.

SUMMARY OF THE INVENTION

We have discovered, and characterized by sequence, DNA segments which are response elements operative to confer responsiveness to retinoic acid, or derivatives thereof, on the transcriptional activities of promoters in cells. We have also discovered that the transcriptional activity enhancing effect of the invention response elements occurs in all mammalian cells in the presence of retinoic acid or derivatives thereof, indicating that retinoic acid receptor, or retinoid X receptor, or other orphan receptors recognized by the invention response elements are present endogenously in all of these cells.

Contrary to what is reported in the art for the GRE, ERE and TRE, the novel response elements disclosed herein have a tandem repeat sequence, as opposed to a palindromic sequence reported for GRE, ERE and TRE. In addition, the invention response elements are much less susceptible to transcriptional activation by non-cognate receptors (e.g., estrogen receptor (ER), GR, thyroid hormone receptor (TR), etc.) than are the known response elements (GRE, ERE, TRE).

By using transcriptional control regions comprising response elements of the present invention and a functional promoter, it is now possible to provide recombinant DNA vectors containing a gene, the transcription (and, thereby, also expression) of which is under the control of a promoter, the transcriptional activity of which is responsive to (and increased by) retinoic acid or derivatives thereof.

DETAILED DESCRIPTION OF THE INVENTION

Figure 1:
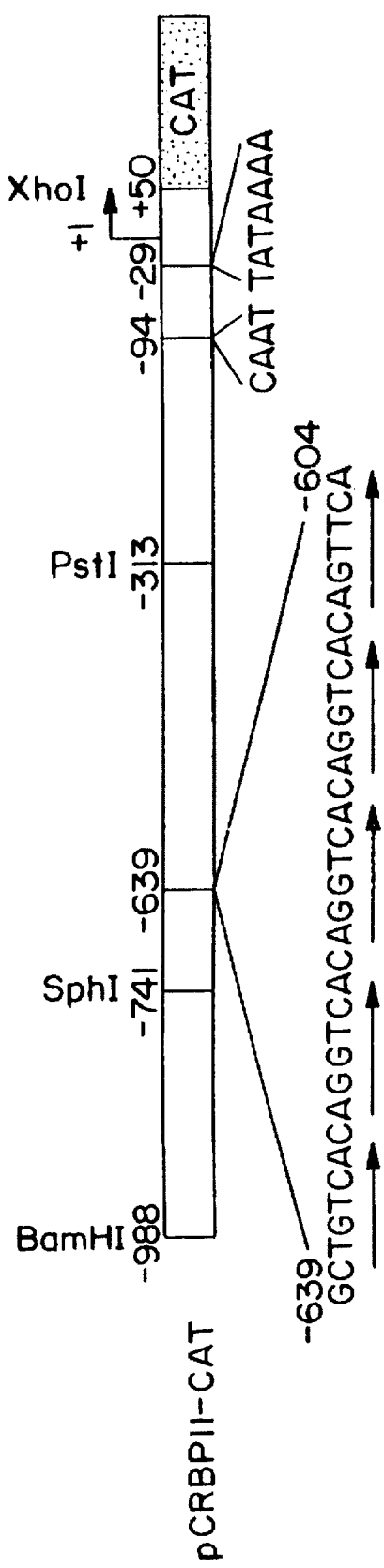
FIG. 1 presents a schematic diagram of a portion of the pCRBPII-CAT reporter plasmid (see also SEQ ID NO:1).

In accordance with the present invention, there is provided a substantially pure DNA having the sequence:

5'—NNNNNN—(N—NNNNNN)$_x$—3'   (SEQ ID NO:2), wherein each N is independently selected from A, T, C, or G; with the proviso that at least 3 nucleotides of each —NNNNNN— group of nucleotides are identical with the nucleotides at comparable positions of the sequence —AGGTCA—, and x is a whole number of at least 1.

Alternatively, the invention response elements can be described as substantially pure DNA having the sequence:

5'—AGGTCA—(N—AGGTCA)$_x$—3'   (SEQ ID NO:3), wherein N and x are as defined above, and up to 3 nucleotides of each —GGTCA— group of nucleotides can be replaced with N.

In accordance with another embodiment of the present invention, there are provided DNA constructs comprising the above-described response elements operatively linked to a promoter which is not normally subject to transcriptional activation by retinoic acid or derivatives thereof; wherein the DNA and the promoter are operatively linked so as to confer transcriptional activation activity on said promoter in the presence of a suitable ligand and its associated receptor. The above-described constructs can then be operatively linked to a gene for transcription. The resulting gene-containing DNA construct can then be incorporated into a vector for expression. The resulting vector can then be transformed into suitable host cells.

Cells containing the above-described vectors can then be used for the controlled expression of a gene of interest, in response to the presence or absence of a suitable ligand and its associated receptor.

In accordance with yet another embodiment of the present invention, there is provided a method for testing the activity of a test compound as an agonist of retinoic acid (or derivatives thereof), said method comprising:

(a) culturing a cell (as described above) in the presence of a retinoid receptor, and in the further presence, or in the absence, of the test compound; and thereafter (b) comparing the amount of the protein of interest expressed during the culturing in the presence, or in the absence, of the test compound.

In accordance with still another embodiment of the present invention, there is provided a method for testing the activity of a test compound as an antagonist of retinoic acid (or derivatives thereof), said method comprising:

(a) culturing a cell (as described above) in the presence of a retinoid receptor and retinoic acid (or derivatives thereof), and further:
  (i) in the presence of the test compound, or
  (ii) in the absence of the test compound; and thereafter (b) comparing the amount of the protein of interest expressed during the (i) and (ii) culturing steps.

In accordance with a further embodiment of the present invention, there is provided a method to distinguish whether or not responsiveness to retinoic acid or derivatives thereof occurs via a pathway unique to RXR, relative to RAR, said method comprising:

contacting a vector containing an invention response element (as described above) with retinoic acid or derivatives thereof, and varying ratios of RAR:RXR expression vectors, and thereafter determining the effect of increasing ratios of RAR:RXR on transcription activation of said response element by retinoic acid or derivatives thereof.

In accordance with a still further embodiment of the present invention, there is provided a method to modulate RXR-induced expression in cells, said method comprising administering to said cells an amount of RAR effective to competitively bind, in the presence of retinoic acid or derivatives thereof, the response elements of the present invention, in preference to the binding thereof by RXR to the same DNA.

In accordance with another aspect of the present invention, there is provided a method to screen compounds to identify those compounds which act as ligands for orphan receptors, said method comprising:

contacting said compound with cells (as described above), wherein said cells are further transfected with an expression vector for an orphan receptor, wherein said orphan receptor, in the presence of its cognate ligand, is capable of binding to response elements of the present invention, and thereafter assaying for the expression of the reporter protein.

In the present specification and claims, reference is made to phrases and terms of art which are expressly defined for use herein as follows:

"RARβ" or "βRAR" both refer to retinoic acid receptor beta;

"CAT" means chloramphenicol acetyl transferase;

"LUC" means firefly luciferase;

"β-Gal" means β-galactosidase;

"COS" means monkey kidney cells which express T antigen (Tag) [see, for example, Gluzman in Cell, 23:175 (1981)];

"CV-1" means mouse kidney cells from the cell line referred to as "CV-1". CV-1 is the parental line of COS. Unlike COS cells, which have been transformed to express SV40 T antigen (Tag), CV-1 cells do not express T antigen;

"transcriptional control region" or "transcriptional control element" refer to a DNA segment comprising a response element operatively linked to a promoter to confer ligand responsiveness to transcriptional activity of the promoter;

"operatively linked" means that the linkage (i.e., DNA segment) between the DNA segments so linked is such that the described effect of one of the linked segments on the other is capable of occurring. Effecting operable linkages for the various purposes stated herein is well within the skill of those of ordinary skill in the art, particularly with the teaching of the instant specification;

"promoter being naturally unresponsive to ligand" means that ligand does not enhance transcription from the promoter to an observable extent in a cell (e.g., a mammalian cell) unless a response element of the invention is spliced or inserted (upstream of the promoter) relative to the direction of transcription therefrom, by recombinant DNA or genetic engineering methods, into a DNA segment comprising the promoter, and linked to the promoter in a manner which makes transcriptional activity from the promoter operatively responsive to ligand;

"substantial sequence homology" refers to DNA or RNA sequences which have de minimus sequence variations from, and retain the same functions as, the actual sequences disclosed and claimed herein;

"retinoid receptors" refers to members of the steroid/thyroid superfamily of receptors which, in combination with retinoic acid, or derivatives thereof (as broadly defined herein), are effective to transcriptionally activate the response element(s) of the present invention, e.g., the retinoid X receptor [see, for example, Mangelsdorf, et al., in Nature 345:224–229 (1990], the ultraspiracle receptor [see, for example, Oro et al., in Nature 347:298–301 (1990)], and the like;

"orphan receptors" refers to identified members of the steroid/thyroid superfamily of receptors for which specific ligands have not yet been identified. Examples include HNF4 [see, for example, Sladek et al., in Genes & Development 4:2353–2365 (1990)], the COUP family of receptors [see, for example, Miyajima et al., in Nucleic Acids Research 16:11057–11074 (1988), Wang et al., in Nature 340:163–166 (1989)], COUP-like receptors and COUP homologs, such as those described by Mlodzik et al., in Cell 60:211–224 (1990) and Ladias et al., in Science 251:561–565 (1991), the ultraspiracle receptor (see, for example, Oro et al., supra), and the like;

"suitable ligands" for hormone receptors refers to the specific ligand(s) which, in combination with its cognate receptor, is effective to transcriptionally activate the response element to which the cognate receptor binds;

"retinoic acid (RA) or derivatives thereof" refers broadly to retinoid compounds, including analogs and derivatives thereof, as described, for example, in *The Retinoids*, Volumes 1 and 2, Sporn, Roberts & Goodman, eds., Academic Press, Inc., New York (1984).

The nucleotides which occur in the various nucleotide sequences appearing herein have their usual single-letter designations (A, G, T, C or U) used routinely in the art.

In the present specification and claims, references to Greek letters may either be written out as alpha, beta, etc. or the corresponding Greek letter symbols (e.g., α, β, etc.) may sometimes used.

The response elements of the present invention can be composed of two or more "half sites", wherein each half site comprises the sequence —NNNNNN—, with the proviso that at least 3 of the nucleotides in the half-site sequence are identical with the nucleotides at comparable positions of the sequence —AGGTCA—. Where one of the half sites varies by 3 nucleotides from the preferred sequence of —AGGTCA—, it is preferred that the other half site of the response element vary from the preferred sequence by less than 3 nucleotides. It is presently preferred that the 3'-half site (or downstream half site) of each pair of half sites vary from the preferred sequence by at most 1 nucleotide.

Exemplary response elements contemplated by the present invention are derived from various combinations of half sites having sequences selected from, for example, —AGGTCA—, —AGTTCA—, —CTGTCA—, —GGGTCA—, —ATTTCA—, —ATGTCA—, —CGGTCA—, —AGCTCA—, —AGGCCA—, —AGGTGA—, —AGGTTA—, —AGGTCC—, —ATGTCG—, and the like. Presently preferred half sites are those having sequences selected from —AGGTCA—, —AGTTCA—, or —CTGTCA—.

While the spacer nucleotide can be any one of C, T, G, or A, it is presently preferred to use C as the spacer nucleotide, because this is the spacer most commonly observed in response elements found in nature.

Presently preferred response elements contemplated by the present invention include:

5'—AGGTCA—C—AGGTCA—3'                     (SEQ ID NO:4),

5'—AGGTCA—C—AGGTCA—C—AGGTCA—C—AGT-
TCA—3'                                    (SEQ ID NO:5),

5'—CTGTCA—C—AGGTCA—C—AGGTCA—C—AGGTCA—
C—AGTTCA—3'(SEQ ID NO:6), and the like.

With respect to the promoter which is part of a transcriptional control region of the invention, practically any promoter may be used, so long as the transcriptional activity of such a promoter can be enhanced by a response element of the present invention (when suitably positioned upstream from the promoter), provided that such promoter is naturally unresponsive, in its transcriptional activity, to retinoic acid or derivatives thereof. Among such promoters are Delta-MTV promoter of mouse mammary tumor virus, Herpes simplex thymidine kinase (tk) promoter, basal Simian virus SV-40 promoter, the Drosophila alcohol dehydrogenase (ADH) promoter, and the like. Presently preferred are promoters which require a response element for activity.

Virtually any protein or polypeptide of interest can be made with cells transformed with an expression vector of the invention. Such proteins include hormones, lymphokines, receptors or receptor subunits, immunoglobulin chains and the like. Indicator proteins such as LUC, CAT, and β-Gal can also be made.

Among the types of cells that can be transformed in accordance with the invention are mammalian cells, avian cells, insect cells, and the like, such as, for example, CV-1, COS, F9, P19, CHO, HeLa, NIH 3T3, HuTu80, Rat2 fibroblasts, HT1080.T, chick embryo fibroblasts, quail QT6, Drosophila Schneider S2 cells, and the like.

The invention method for determining the activity of a test compound as an agonist or antagonist of retinoic acid or derivatives thereof can be carried out employing standard assay techniques, as are well known by those of skill in the art. See, for example, Mangelsdorf et al., in *Nature* 345:224–229 (1990).

Test compounds contemplated for screening in accordance with the invention assay methods include any compound which can potentially affect the ability of receptor to promote trans-activation through a response element of the present invention.

In accordance with a specific embodiment of the present invention, wherein it is possible to distinguish whether responsiveness to retinoic acid (or derivatives thereof) occurs via a pathway unique to RXR (relative to RAR) or via some other pathway, responsiveness to retinoic acid (or derivatives thereof) via the RAR pathway would result in increased amounts of transactivation as a function of increasing RAR expression, while responsiveness to retinoic acid (or derivatives thereof) via the RXR pathway would result in reduced levels of transactivation as a function of increased RAR expression (reduced levels of transactivation would be caused by RAR progressively blocking activation by RXR).

Receptors, assay methods, and other subject matter pertinent to the subject matter of the present specification may be found in the following references, which are incorporated herein by reference: Commonly assigned United States patent application Ser. No. 108,471, filed Oct. 20, 1987 and published as PCT International Publication No. WO 88,03168; commonly assigned United States patent application Ser. No. 276,536, filed Nov. 30, 1988 and published as European Patent Application Publication No. 0 325 849; commonly assigned United States patent application Ser. No. 370,407, filed Jun. 22, 1989, said Application listing a Budapest Treaty Deposit of a plasmid harboring a cDNA encoding a gamma-retinoic acid receptor, said deposit having been made Jun. 22, 1989, and bearing American Type Culture Collection Accession No. 40623; Zelent et al., *Nature* 339, 714 (1989); Petkovich et al., *Nature* 330, 444 (1987); Brand et al., *Nature* 332, 850 (1988).

Because the DNA segments which comprise the response elements of the present invention are relatively short, they may be provided synthetically, that is by synthesizing the response element-containing oligonucleotide on a DNA synthesizer as is known in the art. It is frequently very desirable to provide restriction endonuclease sites at the 3'- and 5'-ends of the oligomer, such that the synthetic response element may be conveniently inserted into a DNA expression vector at a site upstream from the promoter, whose transcriptional activity is to be enhanced and which drives transcription of the desired gene. As those of ordinary skill in the art will understand, the response elements of the present invention, like other response elements, are orientation and, with wide latitude, position independent. Thus, the response elements of the present invention are functional in either orientation and may be placed in any convenient location from about 30 nucleotides upstream to about 10,000 nucleotides upstream from the promoter to be affected.

Preferred cells for use with expression systems employing transcriptional control regions comprising invention response element are mammalian cells such as COS cells and CV-1 cells. COS-1 (referred to as COS) cells are mouse kidney cells that express SV40 T antigen (Tag); while CV-1 cells do not express SV40 Tag. CV-1 cells are convenient because they lack any endogenous glucocorticoid or mineralocorticoid or other known steroid or thyroid hormone receptors, except that they do produce low levels of βRAR. Thus, via gene transfer with appropriate expression vectors comprising a heterologous gene under the control of a transcriptional control region of the invention, it is possible to convert these host cells into transformed cells which produce increased quantities of a desired protein in response to induction by retinoic acid or derivatives thereof.

Expression plasmids containing the SV40 origin of replication can propagate to high copy number in any host cell which expresses SV40 Tag. Thus, expression plasmids carrying the SV40 origin of replication can replicate in COS cells, but not in CV-1 cells. Although increased expression afforded by high copy number is desirable, it is not critical to the assay systems described herein. The use of any particular cell line as a host is also not critical, although CV-1 cells are presently preferred because they are particularly convenient.

The invention will now be described in detail by reference to the following non-limiting example.

EXAMPLE

Cellular retinol binding protein type II (CRBPII) is an abundant intestinal protein. A portion of the rat CRBPII gene promoter, from position −988 to +50 [see Demmer, et al., in J. Biol. Chem. 262:2425–2467 (1987)], was introduced into a plasmid which would regulate expression of the reporter, bacterial chloramphenicol acetyl transferase (see FIG. 1). The resultant reporter plasmid, pCRBPII-CAT, was tested for retinoic acid (RA) responsiveness after transfection into mouse embryonal teratocarcinoma F9 cells. F9 cells endogenously express high amounts of retinoic acid receptor (RAR), and can efficiently transactivate (>100-fold) a reporter plasmid containing the well characterized RA-inducible promoter of the RARβ gene [see de The et al., in Nature 343:177–180 (1990) and Sucov, et al., in Proc. Natl. Acad. Sci. U.S.A. 87:5392–5396 (1990)]. However, pCRBPII-CAT conferred no basal or RA-inducible CAT activity in these cells. To eliminate the possibility that regulation of the CRBPII promoter requires an augmented concentration of RAR, as is the case for the laminin retinoic acid response element [RARE; see Vasias, et al., in Proc. Natl Acad. Sci. U.S.A. 86:9099–9103 (1989], or that its regulation is isoform specific, expression vectors bearing all three subtypes of RAR were each separately cotransfected with pCRBPII-CAT into F9 cells.

Even after overexpression, RARα, RARβ and RARγ are not able to confer a RA response on pCRBPII-CAT. It was next tested whether this were also true for the retinoid X receptor (RXR). The RXRs are members of the nuclear receptor superfamily which also respond specifically to RA but which are substantially different in primary structure and ligand specificity from the RARs [see Mangelsdorf, et al., in Nature 345:224–229 (1990]. Remarkably, RA provoked a dramatic increase (100-fold) in CAT activity when the expression vector encoding the human RXRα was cotransfected with the pCRBPII-CAT reporter into F9 cells. This induction of the CRBPII promoter by RXR is dependent on both the concentration ligand and the concentration of receptor.

Figure 2:
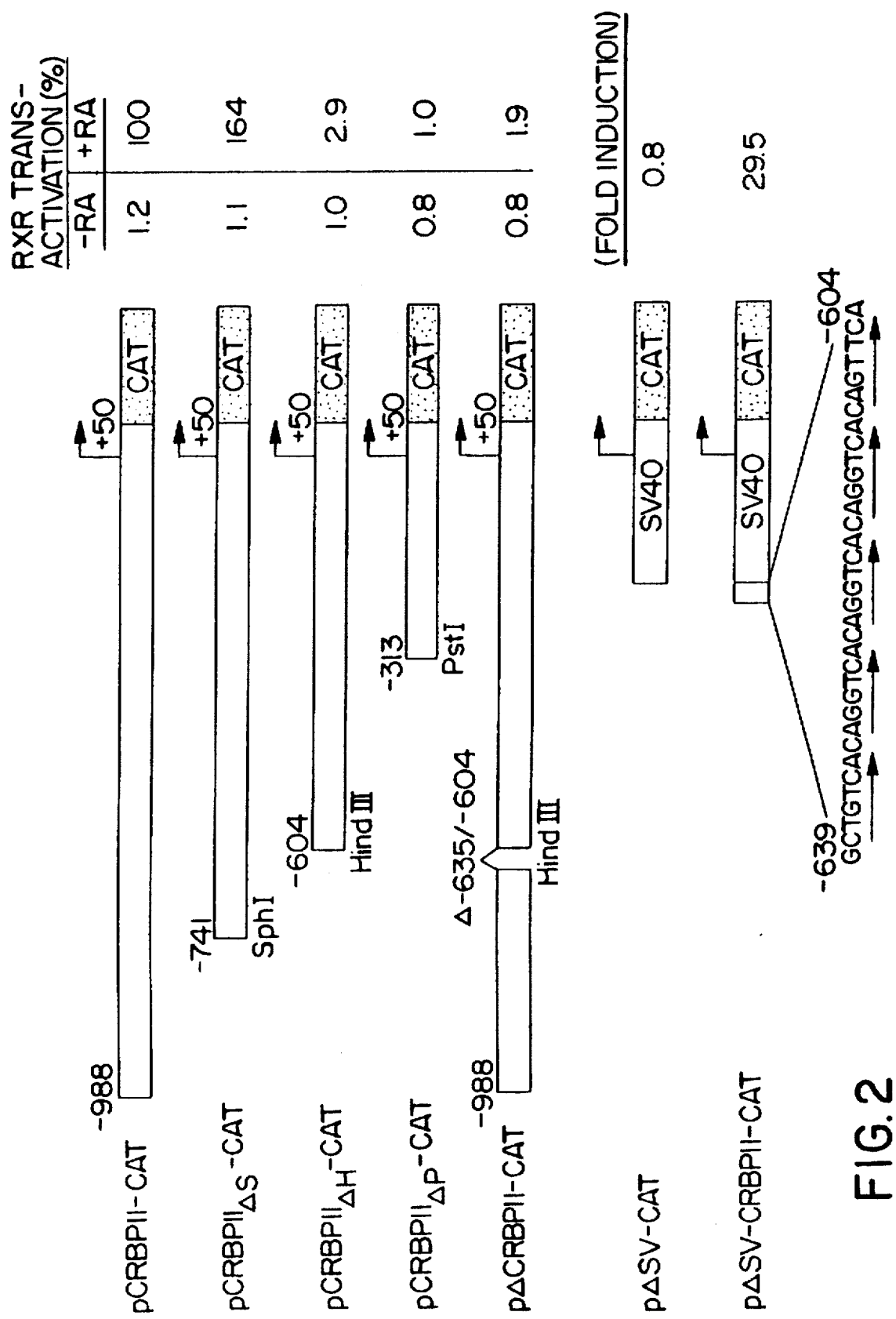
FIG. 2 summarizes transactivation of the response elements of the invention by RXR in the presence and absence of retinoic acid.

To assess the exact sequences within the CRBPII promoter that function as an RXR response element (RXRE), a series of 5'-deletion mutants were constructed starting with the parent reporter plasmid pCRBPII-CAT (see FIG. 2). In the absence of RA, all of these constructs exhibited very low CAT activity in F9 cells cotransfected with RXR. After addition of RA, full RXR-dependent transactivation could still be seen when promoter sequences were deleted to −741 (pCRBPII$_{AS}$-CAT). However, further deletions to −604 (pCRBPII$_{AH}$-CAT) and −313 (pCRBPII$_{AP}$-CAT) abolished this response. These results indicate that an RXRE is located between bases −741 to −604 in the CRBPII gene promoter. Inspection of this region reveals a striking sequence of bases from −639 to −604 which contains five nearly perfect tandem repeats of —AGGTCAC—. Deletion of the sequence including these half-sites (pACRBPII-CAT, FIG. 2) eliminated RXR-dependent induction, providing direct evidence that this sequence functions as an RXRE. Significantly, the CRBPII-RXRE can be fused to an heterologous promoter, such as the minimal SV40 early promoter, and confer RA and RXR dependent activation (see pASV-CRBPII-CAT in FIG. 2; see also below).

To demonstrate that the CRBPII-RXRE is an authentic binding site for RXR, partially purified, bacterially synthesized receptor proteins were examined by gel retardation assays using [$^{32}$P]-labeled DNA probes. As a control, RAR was also included in these studies. Previous work has shown that bacterially produced RAR is competent for both ligand and DNA binding [see Yang, et al., in Proc. Natl. Acad. Sci. U.S.A. 88: in press (1991)]. Surprisingly, when increasing amounts of RAR were incubated with [$^{32}$P] CRBPII-RXRE, a major protein-DNA complex could be formed which eventually saturated all of the labeled probe. The binding affinity of RAR to the RXRE appeared to be even greater than its binding to βRE (a known RARE; see de The, et al., Supra, and Sucov, et al., Supra). In addition, unlabeled CRBPII-RXRE competed at least as well as unlabeled βRE for [$^{32}$p] βRE binding to RAR. The specificity of the RAR for both βRE and CRBPII-RXRE are further demonstrated by the inability of a nonspecific oligonucleotide (GRET) to compete.

When a similar analysis was performed using RXR proteins, another unexpected result was observed. While increasing amounts of RXR bound the CRBPII-RXRE probe strongly and specifically, as expected, the protein-DNA complex which is formed between RXR and the RXRE migrates with a much slower electrophoretic mobility than does the complex formed between RAR and the RXRE (even though both receptors are the same size). Further, the βRE, which is a weak RXR response element and does not compete well with CRBPII-RXRE for RXR binding, also forms a much weaker and faster migrating complex with RXR than does the CRBPII-RXRE. These results indicate that RXR binds to the CRBPII-RXRE as a multimer, whereas the RAR does not. This higher order complex may contribute to the RXR's exclusive ability to transactivate the CRBPII gene promoter. Within the CRBPII-RXRE there are four perfect direct repeats of the canonical half-element —AGGTCA—, each separated by one nucleotide. This suggests that the RXR binds to CRBPII-RXRE as a tetramer.

Figure 3A:
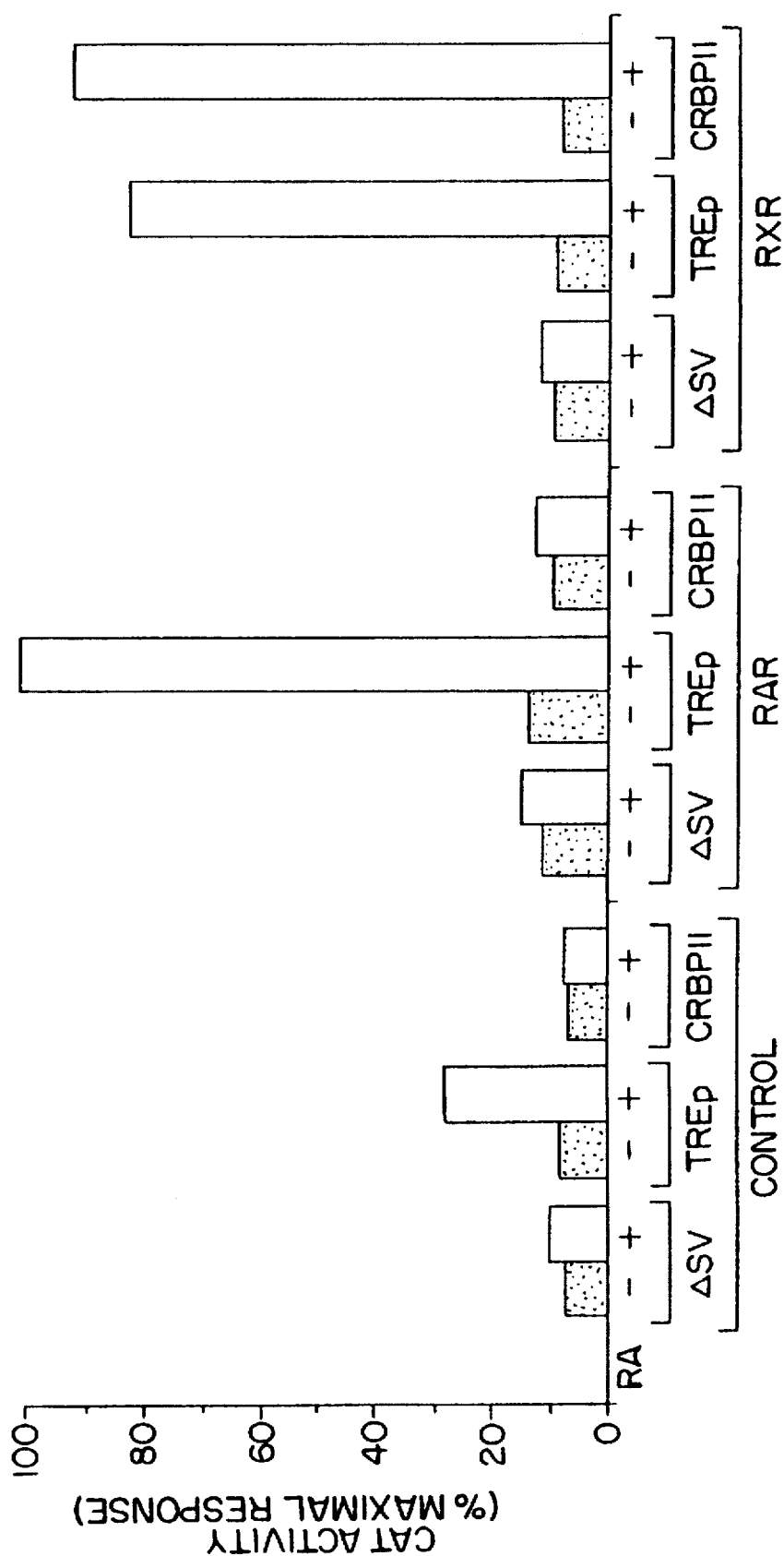
FIG. 3a presents results of cotransfection of CV-1 cells with RAR or RXR expression plasmids and various reporter plasmids.
Figure 3B:
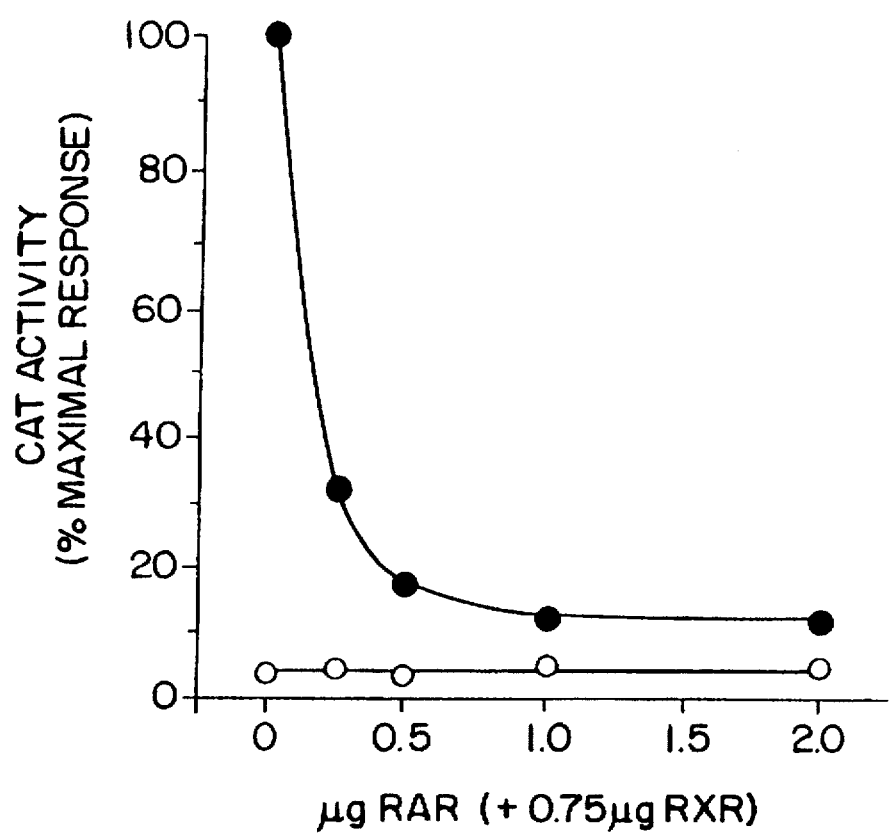
FIG. 3b indicates the ability of RAR to block RXR's ability to transactivate pCRBPII-CAT in the presence (or absence) of retinoic acid. In the Figure, closed circles represent experiments run in the presence of retinoic acid, and open circles represent experiments run in the absence of retinoic acid.

Since RAR tightly binds the CRBPII-RXRE, yet does not transactivate the CRBPII gene promoter, the potential role of RAR in regulating CRBPII expression was investigated. To investigate the specificity of the retinoid receptors for the RXRE, cotransfection studies were performed in CV-1 cells, which, unlike F9 cells, do not express high endogenous levels of RAR. The reporter plasmids used in these experiments were constructed by introducing TRE$_p$, a known RARE and RXRE [see Mangelsdorf, et al., in Nature 345: 224–229 (1990) and Umesono, et al., in Nature 336:262–265 (1988)], and CRBPII-RXRE into the minimal promoter of pΔSV-CAT (K. Umesono and R. Evans, in preparation). As shown in FIG. 3 and as previously demonstrated (Umesono et al., Supra), $TRE_p$ responds markedly to RA in the presence of either RAR or RXR. However, in agreement with experiments on the native CRBPII promoter (FIG. 2), the RXRE is RA-responsive only in the presence of RXR.

It was next tested to see whether the ability of the RAR to bind the RXRE would also enable it to block RXR transactivation. When increasing amounts of RAR expression plasmids were cotransfected with a fixed concentration of RXR expression plasmid, RXR activation decreased dramatically and was 90% suppressed when the concentration of expression vectors for RAR and RXR was equal (see FIG. 3b). These results suggest that vitamin A metabolites are able to feedback regulate the expression of CRBPII and that this regulation can be either positive or negative depending on the type of retinoid receptor present and its concentration. The discovery of the CRBPII-RXRE assigns a specific role to the RXR in modulating vitamin A homeostasis and provides a useful tool for distinguishing between the pathways of RXR and RAR action.

While the invention has been described in detail with reference to preferred embodiments thereof, it will be understood that modifications and variations are within the spirit and scope of that which is described and claimed herein.

That which is claimed is:

1. A substantially pure DNA construct comprising:
   1) a steroid hormone receptor response element having the sequence:

5'—NNNNNN—(N—NNNNNN)$_x$—3' wherein each —NNNNNN— is a half site, —N— is a spacer nucleotide, and X is 4,
   wherein nucleotides at positions 4, 5, and 6 in each half site are nucleotides T, C, and A, respectively, each half site has at least 5 nucleotides corresponding to the sequence —AGGTCA—, and at least two of the half sites are directly tandemly repeated, and
   2) a heterologous promoter,
   wherein the response element is operatively linked to said heterologous promoter.

2. A substantially pure DNA construct comprising:
   1) asteroid hormone receptor response element having the sequence:

5'—NNNNNN—(N—NNNNNN)$_x$—3' wherein each —NNNNNN— is a half site, —N— is a spacer nucleotide, and X is 3,
   wherein nucleotides at positions 4, 5, and 6 in each half site are nucleotides T, C, and A, respectively, each half site has at least 5 nucleotides corresponding to the sequence —AGGTCA—, and at least two of the half sites are directly tandemly repeated, and
   2) a heterologous promoter,
   wherein the response element is operatively linked to said heterologous promoter.

3. A substantially pure DNA construct comprising:
   1) asteroid hormone receptor response element having the sequence:

5'—NNNNNN—(N—NNNNNN)$_x$—3' wherein each —NNNNNN— is a half site, —N— is a spacer nucleotide, and X is 2,
   wherein nucleotides at positions 4, 5, and 6 in each half site are nucleotides T, C, and A, respectively, each half site has at least 5 nucleotides corresponding to the sequence —AGGTCA—, and at least two of the half sites are directly tanderaly repeated, and
   2) a heterologous promoter,
   wherein the response element is operatively linked to said heterologous promoter.

4. A substantially pure DNA construct comprising:
   1) asteroid hormone receptor response element having the sequence:

5'—NNNNNN—N—NNNNNN—3' wherein each —NNNNNN— is a half site, —N— is a spacer nucleotide,
   wherein nucleotides at positions 4, 5, and 6 in each half site are nucleotides T, C, and A, respectively, each half site has at least 5 nucleotides corresponding to the sequence —AGGTCA—, and said half sites are tandemly repeated, and
   2) a heterologous promoter,
   wherein the response element is operatively linked to said heterologous promoter.

5. A substantially pure DNA construct comprising:
   1) asteroid hormone receptor response element having the sequence:

5'—NNNNNN—(N—NNNNNN)$_x$—3' wherein each —NNNNNN— is a half site, —N— is a spacer nucleotide, and X is 1–4,
   wherein the half sites are selected from the group consisting of AGGTCA, AGTTCA, CTGTCA, ATTTCA, ATGTCA, CGGTCA, AGCTCA, AGGCCA, AGGTGA, AGGTTA, AGGTCC, and ATGTCG and
   wherein at least two of the half sites are directly tandemly repeated, and
   2) a heterologous promoter,
   wherein the response element is operatively linked to said heterologous promoter.

6. A substantially pure DNA construct comprising:
   1) a response element having the nucleic acid sequence CTGTCA—C—AGGTCA—C—AGGTCA—C—AGGTCA—C—AGGTCA (SEQ ID NO:6) and
   2) a heterologous promoter,
   wherein the response element is operatively linked to said heterologous promoter.

7. The DNA construct of claim 1, wherein the promoter is selected from the group consisting of delta-MTV promoter of mouse mammary tumor virus, SV40 early gene promoter, Herpes simplex virus thymidine kinase promoter, and Drosophila alcohol dehydrogenase promoter.

8. The DNA construct of claim 2, wherein the promoter is selected from the group consisting of delta-MTV promoter of mouse mammary tumor virus, SV40 early gene promoter, Herpes simplex virus thymidine kinase promoter, and Drosophila alcohol dehydrogenase promoter.

9. The DNA construct of claim 3, wherein the promoter is selected from the group consisting of delta-MTV promoter of mouse mammary tumor virus, SV40 early gene promoter, Herpes simplex virus thymidine kinase promoter, and Drosophila alcohol dehydrogenase promoter.

10. The DNA construct of claim 4, wherein the promoter is selected from the group consisting of delta-MTV promoter of mouse mammary tumor virus, SV40 early gene promoter, Herpes simplex virus thymidine kinase promoter, and Drosophila alcohol dehydrogenase promoter.

11. The DNA construct of claim 5, wherein the promoter is selected from the group consisting of delta-MTV promoter of mouse mammary tumor virus, SV40 early gene promoter, Herpes simplex virus thymidine kinase promoter, and Drosophila alcohol dehydrogenase promoter.

12. The DNA construct of claim 6, wherein the promoter is selected from the group consisting of delta-MTV promoter of mouse mammary tumor virus, SV40 early gene promoter, Herpes simplex virus thymidine kinase promoter, and Drosophila alcohol dehydrogenase promoter.

13. The DNA construct of claim 1 operatively linked to a gene encoding a protein for transcription.

14. The DNA construct of claim 2 operatively linked to a gene encoding a protein for transcription.

15. DNA construct of claim 3 operatively linked to a gene encoding a protein for transcription.

16. The DNA construct of claim 4 operatively linked to a gene encoding a protein for transcription.

17. The DNA construct of claim 5 operatively linked to a gene encoding a protein for transcription.

18. The DNA construct of claim 6 operatively linked to a gene encoding a protein for transcription.

19. The DNA construct of claim 13, wherein said gene is a reporter gene selected from the group consisting of luc, cat, and beta-gal.

20. The DNA construct of claim 14, wherein said gene is a reporter gene selected from the group consisting of luc, cat, and beta-gal.

21. The DNA construct of claim 15, wherein said gene is a reporter gene selected from the group consisting of luc, cat, and beta-gal.

22. The DNA construct of claim 16, wherein said gene is a reporter gene selected from the group consisting of luc, cat, and beta-gal.

23. The DNA construct of claim 17, wherein said gene is a reporter gene selected from the group consisting of luc, cat, and beta-gal.

24. The DNA construct according to claim 18, wherein said reporter gene is selected from the group consisting of luc, cat, and beta-gal.

25. The DNA construct according to claim 19, wherein said reporter gene is cat.

26. The DNA construct according to claim 20, wherein said reporter gene is cat.

27. The DNA construct according to claim 21, wherein said reporter gene is cat.

28. The DNA construct according to claim 22, wherein said reporter gene is cat.

29. The DNA construct according to claim 23, wherein said reporter gene is cat.

30. The DNA construct according to claim 24, wherein said reporter gene is cat.

31. A vector comprising the DNA construct of claim 13.
32. A vector comprising the DNA construct of claim 14.
33. A vector comprising the DNA construct of claim 15.
34. A vector comprising the DNA construct of claim 16.
35. A vector comprising the DNA construct of claim 17.
36. A vector comprising the DNA construct of claim 18.
37. A cell transformed with the vector of claim 31.
38. A cell transformed with the vector of claim 32.
39. A cell transformed with the vector of claim 33.
40. A cell transformed with the vector of claim 34.
41. A cell transformed with the vector of claim 35.
42. A cell transformed with the vector of claim 36.

43. A cell according to claim 37, wherein the cell is selected from the group consisting of mamalian, avian, and insect cells.

44. A cell according to claim 38, wherein the cell is selected from the group consisting of mamalian, avian, and insect cells.

45. A cell according to claim 39, wherein the cell is selected from the group consisting of mamalian, avian, and insect cells.

46. A cell according to claim 40, wherein the cell is selected from the group consisting of mamalian, avian, and insect cells.

47. A cell according to claim 41, wherein the cell is selected from the group consisting of mamalian, avian, and insect cells.

48. A cell according to claim 42, wherein the cell is selected from the group consisting of mamalian, avian, and insect cells.

49. A cell according to claim 43, wherein the cell is selected from the group consisting of CV-1, COS, F9, CHO, HeLa, NIH 3T3, HuTu80, Rat2 fibroblast, HT1080.T, chick embryo fibroblast, quail QT6, and Drosophila Schneider S2.

50. A cell according to claim 44, wherein the cell is selected from the group consisting of CV-1, COS, F9, CHO, HeLa, NIH 3T3, HuTu80, Rat2 fibroblast, HT1080.T, chick embryo fibroblast, quail QT6, and Drosophila Schneider S2.

51. A cell according to claim 45, wherein the cell is selected from the group consisting of CV-1, COS, F9, CHO, HeLa, NIH 3T3, HuTu80, Rat2 fibroblast, HT1080.T, chick embryo fibroblast, quail QT6, and Drosophila Schneider S2.

52. A cell according to claim 46, wherein the cell is selected from the group consisting of CV-1, COS, F9, CHO, HeLa, NIH 3T3, HuTu80, Rat2 fibroblast, HT1080.T, chick embryo fibroblast, quail QT6, and Drosophila Schneider S2.

53. A cell according to claim 47, wherein the cell is selected from the group consisting of CV-1, COS, F9, CHO, HeLa, NIH 3T3, HuTu80, Rat2 fibroblast, HT1080.T, chick embryo fibroblast, quail QT6, and Drosophila Schneider S2.

54. A cell according to claim 48, wherein the cell is selected from the group consisting of CV-1, COS, F9, CHO, HeLa, NIH 3T3, HuTu80, Rat2 fibroblast, HT1080.T, chick embryo fibroblast, quail QT6, and Drosophila Schneider S2.

55. A method for the controlled expression of a gene encoding a protein for transcription, said method comprising culturing the cells of claim 37 in the presence or absence of retinoic acid or derivatives thereof and the receptor therefor.

56. A method according to claim 55, wherein said receptor is RXR.

57. A method for the controlled expression of a gene encoding a protein for transcription, said method comprising culturing the cells of claim 38 in the presence or absence of retinoic acid or derivatives thereof and the receptor therefor.

58. A method according to claim 57, wherein said receptor is RXR.

59. A method for the controlled expression of a gene encoding a protein for transcription, said method comprising culturing the cells of claim 39 in the presence or absence of retinoic acid or derivatives thereof and the receptor therefor.

60. A method according to claim 59, wherein said receptor is RXR.

61. A method for the controlled expression of a gene encoding a protein for transcription, said method comprising culturing the cells of claim 40 in the presence or absence of retinoic acid or derivatives thereof and the receptor therefor.

62. A method according to claim 61, wherein said receptor is RXR.

63. A method for the controlled expression of a gene encoding a protein for transcription, said method comprising culturing the cells of claim 41 in the presence or absence of retinoic acid or derivatives thereof and the receptor therefor.

64. A method according to claim 63, wherein said receptor is RXR.

65. A method for the controlled expression of a gene encoding a protein for transcription, said method comprising culturing the cells of claim 42 in the presence or absence of retinoic acid or derivatives thereof and the receptor therefor.

66. A method according to claim 65, wherein said receptor is RXR.

67. A method for testing the activity of a test compound as an agonist of retinoid X receptor or a receptor that can be activated by retinoic acid or its derivatives, said method comprising:
  (a) culturing a cell according to claim 37 in the presence of retinoid X receptor (RXR), and in the further presence or absence of the test compound, and thereafter
  (b) comparing the amount of protein expressed during the culturing in the presence or in the absence of the test compound.

68. A method for testing the activity of a test compound as an agonist of retinoid X receptor or a receptor that can be activated by retinoic acid or its derivatives, said method comprising:
  (a) culturing a cell according to claim 38 in the presence of retinoid X receptor (RXR), and in the further presence or absence of the test compound, and thereafter
  (b) comparing the amount of protein expressed during the culturing in the presence or in the absence of the test compound.

69. A method for testing the activity of a test compound as an agonist of retinoid X receptor or a receptor that can be activated by retinoic acid or its derivatives, said method comprising:
  (a) culturing a cell according to claim 39 in the presence of retinoid X receptor (RXR), and in the further presence or absence of the test compound, and thereafter
  (b) comparing the amount of protein expressed during the culturing in the presence or in the absence of the test compound.

70. A method for testing the activity of a test compound as an agonist of retinoid X receptor or a receptor that can be activated by retinoic acid or its derivatives, said method comprising:
  (a) culturing a cell according to claim 40 in the presence of retinoid X receptor (RXR), and in the further presence or absence of the test compound, and thereafter
  (b) comparing the amount of protein expressed during the culturing in the presence or in the absence of the test compound.

71. A method for testing the activity of a test compound as an agonist of retinoid X receptor or a receptor that can be activated by retinoic acid or its derivatives, said method comprising:
  (a) culturing a cell according to claim 41 in the presence of retinoid X receptor (RXR), and in the further presence or absence of the test compound, and thereafter
  (b) comparing the amount of protein expressed during the culturing in the presence or in the absence of the test compound.

72. A method for testing the activity of a test compound as an agonist of retinoid X receptor or a receptor that can be activated by retinoic acid or its derivatives, said method comprising:
  (a) culturing a cell according to claim 42 in the presence of retinoid X receptor (RXR), and in the further presence or absence of the test compound, and thereafter
  (b) comparing the amount of protein expressed during the culturing in the presence or in the absence of the test compound.

* * * * *

SEQUENCE LISTING ( 1 ) GENERAL INFORMATION:

( i i i ) NUMBER OF SEQUENCES: 6

( 2 ) INFORMATION FOR SEQ ID NO:1:

( i ) SEQUENCE CHARACTERISTICS:
( A ) LENGTH: 35 base pairs
( B ) TYPE: nucleic acid
( C ) STRANDEDNESS: unknown
( D ) TOPOLOGY: unknown ( x i ) SEQUENCE DESCRIPTION: SEQ ID NO:1:

GCTGTCACAG GTCACAGGTC ACAGGTCACA GTTCA    35

( 2 ) INFORMATION FOR SEQ ID NO:2:

( i ) SEQUENCE CHARACTERISTICS:
( A ) LENGTH: 13 base pairs
( B ) TYPE: nucleic acid
( C ) STRANDEDNESS: unknown
( D ) TOPOLOGY: unknown ( x i ) SEQUENCE DESCRIPTION: SEQ ID NO:2:

NNNNNNNNN NNN    13

( 2 ) INFORMATION FOR SEQ ID NO:3:

( i ) SEQUENCE CHARACTERISTICS:
( A ) LENGTH: 13 base pairs
( B ) TYPE: nucleic acid
( C ) STRANDEDNESS: unknown
( D ) TOPOLOGY: unknown ( x i ) SEQUENCE DESCRIPTION: SEQ ID NO:3:

AGGTCANAGG TCA    13

( 2 ) INFORMATION FOR SEQ ID NO:4:

( i ) SEQUENCE CHARACTERISTICS:
( A ) LENGTH: 13 base pairs
( B ) TYPE: nucleic acid
( C ) STRANDEDNESS: unknown
( D ) TOPOLOGY: unknown ( x i ) SEQUENCE DESCRIPTION: SEQ ID NO:4:

AGGTCACAGG TCA    13

( 2 ) INFORMATION FOR SEQ ID NO:5:

( i ) SEQUENCE CHARACTERISTICS:

( A ) LENGTH: 27 base pairs
( B ) TYPE: nucleic acid
( C ) STRANDEDNESS: unknown
( D ) TOPOLOGY: unknown ( x i ) SEQUENCE DESCRIPTION: SEQ ID NO:5:

AGGTCACAGG TCACAGGTCA CAGTTCA    27

( 2 ) INFORMATION FOR SEQ ID NO:6:

( i ) SEQUENCE CHARACTERISTICS:
( A ) LENGTH: 34 base pairs
( B ) TYPE: nucleic acid
( C ) STRANDEDNESS: unknown
( D ) TOPOLOGY: unknown ( x i ) SEQUENCE DESCRIPTION: SEQ ID NO:6:

CTGTCACAGG TCACAGGTCA CAGGTCACAG TTCA    34